United States Patent
Oh et al.

(10) Patent No.: US 6,168,952 B1
(45) Date of Patent: Jan. 2, 2001

(54) METHOD FOR PRODUCING FLOWERING ORCHIDS IN VITRO

(75) Inventors: Boung-Jun Oh; Igor Kostenyuk, both of Kwangju (KR)

(73) Assignee: Korea Kumho Petrochemical Co., Ltd., Seoul (KR)

( * ) Notice: Under 35 U.S.C. 154(b), the term of this patent shall be extended for 0 days.

(21) Appl. No.: 09/128,666

(22) Filed: Aug. 4, 1998

(51) Int. Cl.⁷ ............................. C12N 5/00; A01B 79/00
(52) U.S. Cl. ..................... 435/430; 435/420; 435/430.1; 47/58.1
(58) Field of Search ................. 435/430, 430.1, 435/420; 47/58.1

(56) References Cited

PUBLICATIONS

Murashige, et al., A Revised Medium for Rapid Growth and Bio Assays with Tobacco Tissue Cultures (1962) Physiol. Plant., vol. 15 pp. 473–497.

Kerbauy, *Plant Science Letters*, 35(1984), pp. 73–75.
Bonnet–Masimert, *Plant Growth Regulation*, 6(1987), pp. 13–35.
Dickens, *S. Afr. J. Bot.*, 54:4(1998), pp. 325–344.
Wang, et al., *Biotechnology in Agriculture*, 1993, pp. 373–378.
Duan, et al., *Scientia Horticulture*, 59(1994), pp. 253–264.
Duan, et al., *Plant Cell. Tissue and Organ Culture*, 43(1995), pp.71–74.

*Primary Examiner*—Leon B. Lankford, Jr.
(74) *Attorney, Agent, or Firm*—Kenyon & Kenyon

(57) ABSTRACT

An improved method for producing flowering orchid plants by tissue culture is provided. The improvement comprises regenerating orchid plants from rhizome in a medium supplemented with cytokinin, i.e. BA 10 $\mu$M, or auxin, i.e. NAA 20 $\mu$M, or without plant growth regulators and culturing orchid plants without roots which are excised prior to transfer to subsequent medium containing high cytokinin content, i.e. 20–50 $\mu$M, low nitrogen content 3 mM, high phosphorus content, i.e. 6.25 mM, for about 1 to 3 months under the 16/8 hours light/dark photoperiod.

9 Claims, No Drawings

METHOD FOR PRODUCING FLOWERING ORCHIDS IN VITRO

BACKGROUND OF THE INVENTION

1. Field of the Invention

The present invention relates to a method for the floral induction of orchid plants grown aseptically using in vitro system. It can be used for the application of biotechnological purposes and for orchid hybrid breeding.

2. Description of Related Art

Orchids are well-known to have long-time juvenile stage after seed germination and after in vitro plant regeneration. It takes from about couple of years up to 10–13 years to get flowering orchid plant from the seed. Due to various variability in orchids living forms and specific biological properties of different species, hybrids, varieties and cultivars, there is no uniform methodology and even approach to make the juvenile period short and to induce orchid flowering with commercially employed ones. Various treatments were applied traditionally by farmers and researchers using the treatments of long/short day regimens, chilling, high temperature, phytohormone, retardants or specifically designed chemicals etc. to orchid plants. Nevertheless those approaches mentioned above are partially effective for mature orchid plants. In vitro techniques was proved to be applicable for controlling blooming process in higher plants, at least, at certain cases.

Several reports to produce precocious flowering in in vitro system have been published. One of the most efficient methods inducing in vitro orchid flowering was described by Wang et al (1993). This method was applied to *Dendrobium candidum* and includes the following steps:

(A) Protocorm, shoots (without roots) and plantlets (with roots) were obtained from 4–5 months old surface sterilized mature capsules;

(B) These explants mentioned in (A) are transferred to the medium containing abscisic acid (ABA) for two months;

(C) Pre-induced explants were cultured in the medium containing 6-benzyladenine to induce flower bud formation for about 5 months.

In the second method (Duan and Yazawa 1995), three main steps were employed with:

(A) Adventitious shoots formed from nodal sections of floral stalks of Phalaenopsis;

(B) Propagation and growth of floral stalk derived from shoots on Hyponex medium;

(C) Induction of floral bud formation on Vacin-Went medium containing 6-benzyladenine using 9 month old Phalaenopsis shoots.

SUMMARY OF THE INVENTION

An object of the present invention is to provide a method for inducing in vitro early flowering orchids regenerated from the specific vegetative form named rhizome or protocorm like bodies (PLB). This is achieved by 3–4 month old orchid plants regenerated from rhizome and PLB with root excision. Those explants with root excision were cultured on the medium containing low nitrogen content, enhanced phosphorus content and 6-benzyladenine.

Further scope of the applicability of the present invention will become apparent from the detailed description provided below.

DETAILED DESCRIPTION OF THE INVENTION

The following detailed description is provided to help in practicing the present invention. As employed below, the phrase "low nitrogen" preferably denotes that the total nitrogen content is between about 2 mM and 8 mM, and the most preferable one is about 3 mM.

"High phosphorus" denotes that the total phosphorus content is between about 3 mM and 9 mM, and the most preferable one is 6.25 mM.

"Root excision" denotes that plant roots are cut off about 95% to 100% of roots, and the most preferable ones are cut off 100% of roots.

Step (1) Orchid rhizome and PLB are cultured on Murashige and Skoog (MS) medium (1962) supplied with auxins, at 25–28° C., under an illumination of 4,000–8,000 lux, for 14–18 hours a day. The medium can be MS medium, containing 4% (w/v) of sucrose, pH 5.7. This medium is hereinafter referred to as "plant growing medium". Linsmayer and Skoog's medium (Linsmayer and Skoog 1965), Eriksson's medium (Eriksson 1965), and other standard plant tissue culture and orchid media can also be employed in place of "MS medium". Of sugars as carbon source in the medium, glucose, fructose, maltose etc, can be employed in place of sucrose. The sugar concentration can be in the range from 3–6%, preferably 4%, and the pH can be in the range from 4–8, preferably 5.2–6.5. The number of explants can be 1–50, preferably 20–30 per liter. The volume of vessel may be 0.3–1.0 liters, and the volume of medium per 1 liter vessel can be 0.1–0.4 liters, preferably 0.25–0.3 liters.

Step (2) Then the resulted explants are transferred to MS medium supplemented with cytokinin or cytokinin and auxin with high cytokinin/auxin ratio to regenerate plants. The young plants regenerate from the rhizome 90–150 days after transfer to the medium.

Step (3) The resulted about 3 to 4 months old plants undergo root excision and are transferred to the fresh medium containing low nitrogen, high phosphate and cytokinin. Of cytokinins in the medium, 6-benzylaminopurine, kinetin, zeatin, thidiazuron or other routinely applied cytokinins can be employed, preferably 6-benzylaminopurine. The concentration of cytokinin can be in the range from 10–50 $\mu$M, preferably 35–45 $\mu$M. Photoperiod and temperature regimen should be the same as in the first step. The explants are planted in the range from 1 to 5, preferably 2 per 1 liter vessel. In the step mentioned above, orchid plants eventually change vegetative growth to reproductive development displaying producing flower stalks with flower buds.

Step (4) In 1.5–3 months from the beginning of the previous step, the resulted induced plants should be transferred to the medium containing about 20–40 mM, preferably 30 mM of total nitrogen, high phosphate, and cytokinin, preferably, 6benzyladenine. The concentration of cytokinin can be in the range 0–40 $\mu$M, preferably 22 $\mu$M.

Plants cultured on the medium mentioned above develop flowers and can posses fruit onset with self pollination within about 30 to 90 days after the combined treatment. The resulted plants can be used for the purposes of orchid hybrid breeding and for the development of commercial product using flowering orchid plants in tissue culture vessel.

Differences Between the Present Invention and Prior Art Methods

A characteristic feature of the present invention is that aseptically regenerated and cultured orchid plants undergoing root excision are efficiently induced to flowering in vitro when being transferred on medium containing low nitrogen, high phosphate and cytokinin. Fully developed flowers and fruit onset can be reached when pre-induced plants are cultured on medium containing higher nitrogen content and lower cytokinin concentration.

In the first method described, the sterilized mature capsules were used as a source of protocorm, shoots and plantlets for the further induction of in vitro flowering. Thus, the idea to use specific vegetative form (PLB or rhizome) already cultured in vitro for a long time as a source for rapidly and numerous regenerated plants is out of consideration. The same point can be equally applied to the second method described.

Neither the first nor the second method did not employ root excision. Instead, they operated with immature rootless plants exposing them to appropriate treatments. Alternatively, both methods were not able to induce flowering when orchids had fully developed root.

In the first method, the idea to reduce total nitrogen content was not conducted. Although the second method employed low nitrogen content, the lowest concentration was mentioned at the level of 4.5 mM. However, in our experiments, the highest efficiency of orchid flowering induction was achieved at 3.0 mM of total nitrogen (33% lower than that in the first method described).

In both analogous methods described, no orchid species regenerated from rhizome was induced to flowering in vitro. Also, no fruit onset with self pollination has been reported. In order to produce flowers in orchids in vitro, both methods took over 12 months.

The method of present invention allows to overcome drawbacks mentioned above. Although the method of the present invention includes the combined treatments of conventional methods, and each of those methods is known to promote flower bud formation and flower evocation in certain species under particular conditions, the said method comprises 4 steps and employs orchid rhizome and PLB which can be propagated in unlimited scales prior to select them for induction of in vitro flowering. The first step of the present invention comprises micropropagation of rhizome or PLB and plant regeneration. The regenerated plants develop normal leaves and roots. In the second step, the roots are being cut without any injury of the bottom part of orchid plant. In the third step of present invention, rootless plants are transferred to inductive medium which rapidly changes developmental patterns in favor of reproductive stage. Orchid plants develop flower stalks with flower buds. And, in the final step the resulted induced plants are cultured in the medium supplying more nitrogen and less cytokinin. Pre-induced plants mentioned above develop flowers and fruits in the last step.

Effects of the Present Invention

Increase of the flowering induction of orchid plants. Short-time to produce flowering orchid plant in vitro. The possibility to use long-time cultured vegetative form of rhizome and PLB as a source of plants material inducing to bloom. Fruit set in vitro with self pollination.

The efficiency of induction of flowering orchid plants in vitro by the method of present invention is higher than that of the first and second conventional methods (see Table 1). In both previous methods, the regenerated orchid plants were directly transferred to inductive medium or pre-cultured in the medium containing ABA without the combined treatments of root excision, increased phosphorus and reduced nitrogen displayed in the present invention. Although the frequency of flower bud formation was the same in both conventional methods (about 82%), the duration of treatment in the first method was 90 days longer than that in the second method. In addition, the first method included pre-induction in the medium containing ABA as one additional step. Once this additional step was omitted, the average of flowering explants dropped to 45.8%. In the second method, the importance of lowered total nitrogen was emphasized, nevertheless the used nitrogen concentration in second method was 50% higher than that in the present invention. The method of the present invention allowed to induce to flowering nearly 100% of plants treated.

According to the embodiment of the present invention wherein specific vegetative form of orchids cultured in vitro, either rhizome or PLB are employed to regenerate plants needed for flowering induction. Prior to be selected for plant regeneration, the mentioned rhizome or PLB may be propagated through conventional procedure without any limitation to the number of passages. Unlikely in the present invention, both methods described the usage of mature capsules for *D. candidum* and flower stalks for Phalaenopsis as a source for aseptic plants. Therefore, it is not clear whether those methods could induced flowering when either rhizome or PLB are used for regenerating plants.

According to the embodiment of the present invention, wherein 3–4-months old plants with fully developed roots are employed for flowering induction. By the combined treatment of root cutting, cytokinin, lowered total nitrogen and enhanced total phosphorus, the efficiency of flowering induction was much higher than that of flowering induction obtained from the first and second methods.

According to the embodiment of the present invention, wherein "low nitrogen" medium was used instead of "higher nitrogen" medium, the less nitrogen supply resulted in developing multiple flower stalks and at least 1 to 3 flowers in orchid plants tested. Further, the fruit onset was achieved by self pollination in the present invention, whereas no fruit development was mentioned in both conventional methods.

According to the embodiment of the present invention, wherein two-stage cultivation (flower stalk development and flower evocation) of explants were employed, the entire duration of flowering induction is about 90 days which is significantly shorter than in both conventional methods and much shorter than that in ex vitro plants. Therefore, the method of the present invention overcomes the long juvenility of orchids, possesses the reliable approach to induce precocious orchid flowering in vitro at high efficiency, and obtain fruits and seed in sterile conditions.

EXAMPLE 1

Influence of the Combined Application of Root Excision, Cytokinin, Low Nitrogen, and High Phosphorus in Orchid Flowering in vitro.

Aseptically grown *Cymbidium niveo-marginatum* plants were regenerated from rhizome cultured in MS medium supplemented with 40 g/l sucrose and 5 mg/l auxin (1-naphtalene acetic acid) or 1–5 mg/l cytokinin (6-benzyladenine). The Cymbidium rhizome was cultured in the same media in rectangular glass vessel having 1 liter of inner volume and dimensions of 11×9.5×17 cm which contained 250 ml of medium. Such vessels are hereinafter referred to as "1L-vessels". Regenerating plants were cultured during about 3–4 months until they reached 10–14 cm high and developed their root system. Then, the following treatments from a) to d) were carried out.

(a) As mentioned in the present invention, Roots were cut off and the rootless plants were transferred to those 1L-vessels containing inductive medium: MS basal micro and macro salts except nitrogen and phosphorus containing macro salts; total nitrogen content was adjusted to 3 mM, total phosphorus content was adjusted to 6.25 mM; 40 g/l sucrose; 10 mg/l cytokinin (6-benzylaminopurine). The said plants were cultured during 90 days to induce the process of transition to flowering.

(b) As mentioned in the first conventional method, regular MS medium supplemented with 2.0 mg/l 6benzylaminopurine was used to induce flowering in regenerated orchid plants.

(c) As mentioned in the second conventional method, the same treatment as indicated in b) except 10 mg/l 6benzylaminopurine.

(d) Plants were transferred to regular MS medium supplemented (internal control) with 40 g/l sucrose.

In all cases Cymbidium orchid plants were cultured under 16 hours of light (4,000 lux) at temperature 26–28 °0 C. per day. Gelrite (Duchefa, Holland) was employed as a solidifying agent. These data are displayed in Table 1.

TABLE 1

Effects of various treatments for flower induction in *Cymbidium niveo-marginatum* in vitro

| Method | Number of induced plants (%) Days after treatment | | |
|---|---|---|---|
| | 30 | 60 | 90 |
| a) Present Invention Root Excision Cytokinin Low nitrogen High phosphorus | 44.5 | 83.5 | 95.5 |
| b) First conventional method MS medium + BA 2.0 1$^{-1}$ | 0 | 0 | 0 |
| c) Second conventional method MS medium + BA 10.0 1$^{-1}$ | 0 | 0 | 0 |
| d) Internal control Basal MS medium | 0 | 0 | 0 |

It demonstrated that more than 40% of explants on the inductive medium in the present invention for 30 days of cultivation were induced to flowering and flower stalk formation. Whereas both conventional methods including internal control did not produce any flowering explant. The flowering induction of orchid plants in the present invention was 3 times higher than that in the second method 60 days after treatment. Finally, within 90 days nearly 100% of in vitro orchid plants in the present invention revealed various signs of transition to flowering, such as flower stalk, flower bud formation, and flower evocation. Meanwhile, both conventional methods were definitely behind. No flowering orchid plants were observed in the basal MS medium as the internal control.

EXAMPLE 2

Influence of Various Combined Treatments with Several combinations in Orchid Flowering in vitro.

TABLE 2

Effects of various treatments applied in several combinations for flower induction in *Cymbidium niveo-marginatum* in vitro ( − = no treatment, + = treatment)

| Treatment | N$^a$ (mM) | P$^b$ (mM) | RE$^c$ | BA (mg/L) | Number of induced plants (%) Days after treatment | | |
|---|---|---|---|---|---|---|---|
| | | | | | 30 | 60 | 90 |
| MS-control | 60 | 1.25 | − | − | 0 | 0 | 0 |
| A | 3 | 6.25 | + | 10 | 47.5 | 87.5 | 97.5 |
| B | 60 | 1.25 | + | 10 | 45.0 | 75.0 | 94.7 |
| C | 3 | 6.25 | − | 10 | 22.5 | 52.5 | 92.6 |
| D | 3 | 6.25 | + | − | 2.6 | 5.2 | 5.2 |
| E | 3 | 6.25 | − | − | 0 | 0 | 0 |
| F | 60 | 1.25 | − | 10 | 0 | 26.9 | 38.5 |
| G | 60 | 1.25 | + | − | 0 | 0 | 0 |

$^a$total nitrogen content
$^b$total phosphorus content
$^c$root excision

The invention being herein described, it will be obvious that the same may be varied in many ways. Such variations can not be regarded as a departure from the spirit and scope of the invention, and all such modifications as would be obvious to one skilled in the art are intended to be included within the scope of the following claims.

What is claimed:

1. A method for producing in vitro flowering orchid plants, said method comprising regeneration of orchid plants from rhizome in a medium containing cytokin or auxin followed by root excision in regenerated plants and culturing in a medium containing 10–50 μM cytokin, 2–8 mM nitrogen and 3–9 mM phosphorus in a light/dark photoperiod, wherein the improvement comprises:

(a) regenerating orchid plants from rhizome in a medium containing 2–5% w/v sugar and cytokinin (BA) 5–10 μM or auxin (NAA) 10–20 μM under an illumination regimen of about 14 to about 18 hours per day for about 3 to about 5 months;

(b) root excision in the resulting regenerated orchid plants so that not more than about 0.1% to about 1.% of root biomass remains;

(c) culturing the resulting plants from step (b) in a medium containing 3–4% w/v sugar, 20–50 μM cytokin (6-benzylaminopurine), 2–6 mM total nitrogen, 2–8 mM total phosphorus for about 30 to about 100 days under an illumination regimen of about 14 to about 18 hours per day to produce induced plants comprising flower stalks with flower buds; and (d) culturing the induced plants in a medium contaiining 3–4% w/v sugar, 5–50 μM 6-benzylaminopurine, 10–60 mM total nitrogen, 4–8 mM total phosphorus for about 20 to about 40 days under the illumination regimen of about 12 hours to about about 20 hours per day to develop said flowers.

2. The method of claim 1, wherein said sugar of step (a), step (c) and step (d) is at least one member selected from the group consisting of sucrose, glucose, fructose, and maltose.

3. The method of claim 1, wherein said cytokinin is at least one member selected from the group consisting of adenine, adenine hemisulfate, 6-benzylaminopurine, 6-benzylaminopurine riboside, kinetin, kinetin riboside, thidiazuron, zeatin, zeatin riboside.

4. The method of claim 1, wherein said cytokinin of step (a), step (c), and step (d) is 44 μM 6-benzylaminopurine.

5. The method of claim 1, wherein said medium of step (a), step (c), and step (d) is a member selected from the group consisting of Murashige and Skoog's medium containing 4% w/v sucrose at pH 5.70.

6. The method of claim 1, wherein said nitrogen source of step (a), step (b), and step (c) is a member selected from the group consisting of sodium nitrate ($NaNO_3$), potassium nitrate ($KNO_3$), calcium nitrate ($Ca(NO_3)_2$), and ammonium nitrate ($NH_4NO_3$).

7. The method of claim 1, wherein said phosphorus source of step (a), step (c), and step (d) is a member selected from the group consisting from potassium dihydrogen phosphate ($KH_2PO_4$), potassium hydrogen phosphate ($K_2HPO_4$), sodium dihydrogen phosphate ($NaH_2PO_4$), sodium hydrogen phosphate ($Na_2HPO_4$), ammonium dihydrogen phosphate ($NH_4H_2PO_4$), ammonium phosphate (($NH_4)_3PO_4$).

8. The method of claim 1, wherein said plant is a Cymbidium orchid plant.

9. The method of claim 1, wherein said plant is a Dendrobium orchid plant.

* * * * *